(12) United States Patent  
Ramzipoor et al.

(10) Patent No.: US 6,695,863 B1
(45) Date of Patent: *Feb. 24, 2004

(54) SHEATH FOR AN ADJUSTABLE LENGTH BALLOON

(75) Inventors: Kamal Ramzipoor, Union City, CA (US); James C. Peacock, III, Saratoga, CA (US); Gary Schneiderman, Walnut Creek, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/767,119

(22) Filed: Jan. 8, 1997

Related U.S. Application Data

(63) Continuation of application No. 08/486,385, filed on Jun. 7, 1995.

(51) Int. Cl.[7] .............................................. A61M 29/00
(52) U.S. Cl. ............ 606/194; 604/103.05; 604/103.09; 604/96.01
(58) Field of Search ...................... 606/196, 191–195; 604/96, 97, 98, 103.05, 103.09, 96.01, 524, 526, 527; 600/3, 4

(56) References Cited

U.S. PATENT DOCUMENTS

| | | | |
|---|---|---|---|
| 5,002,558 A | | 3/1991 | Klein et al. ................. 606/192 |
| 5,040,548 A | * | 8/1991 | Yock .......................... 606/194 |
| 5,049,130 A | * | 9/1991 | Powell .................... 604/96.01 |
| 5,222,949 A | * | 6/1993 | Kaldany ................ 604/103.09 |
| 5,246,421 A | | 9/1993 | Saab ............................ 604/96 |
| 5,514,093 A | * | 5/1996 | Ellis et al. ............. 604/103.05 |
| 5,545,209 A | * | 8/1996 | Roberts et al. ........ 604/103.05 |
| 5,549,551 A | * | 8/1996 | Peacock, III et al. ... 604/103.05 |
| 5,628,755 A | * | 5/1997 | Heller et al. ............. 604/96.01 |

FOREIGN PATENT DOCUMENTS

| | | |
|---|---|---|
| EP | 0 553 960 | 8/1993 |
| EP | 0 678 307 | 10/1995 |
| EP | 0 727 194 | 8/1996 |
| WO | WO 95/03082 | 2/1995 |
| WO | WO 95/08965 | 4/1995 |
| WO | WO 96/19256 | 6/1996 |

* cited by examiner

*Primary Examiner*—Julian W. Woo
(74) *Attorney, Agent, or Firm*—Fulwider Patton Lee & Utecht, LLP

(57) ABSTRACT

A dilatation catheter assembly which has a dilatation catheter with a sheath mounted on the catheter shaft having an inner lumen extending in the distal portion of the sheath which is configured to slidably receive at least a portion of the dilatation balloon on the distal end of the catheter. The position of the sheath is fixed with respect to the catheter, e.g. a friction fit or bonded in some manner, before the assembly is inserted into the patient's vasculature with the distal portion of the sheath covering a portion of the balloon but leaving a portion of the balloon uncovered with a length equal to the stenotic region to be dilated so that the entire stenosis can be dilated at the same time. The distal portion of the sheath is preferably formed of a flexible polymeric tube with inelastic reinforcement to prevent substantial expansion thereof when the balloon is inflated.

12 Claims, 3 Drawing Sheets

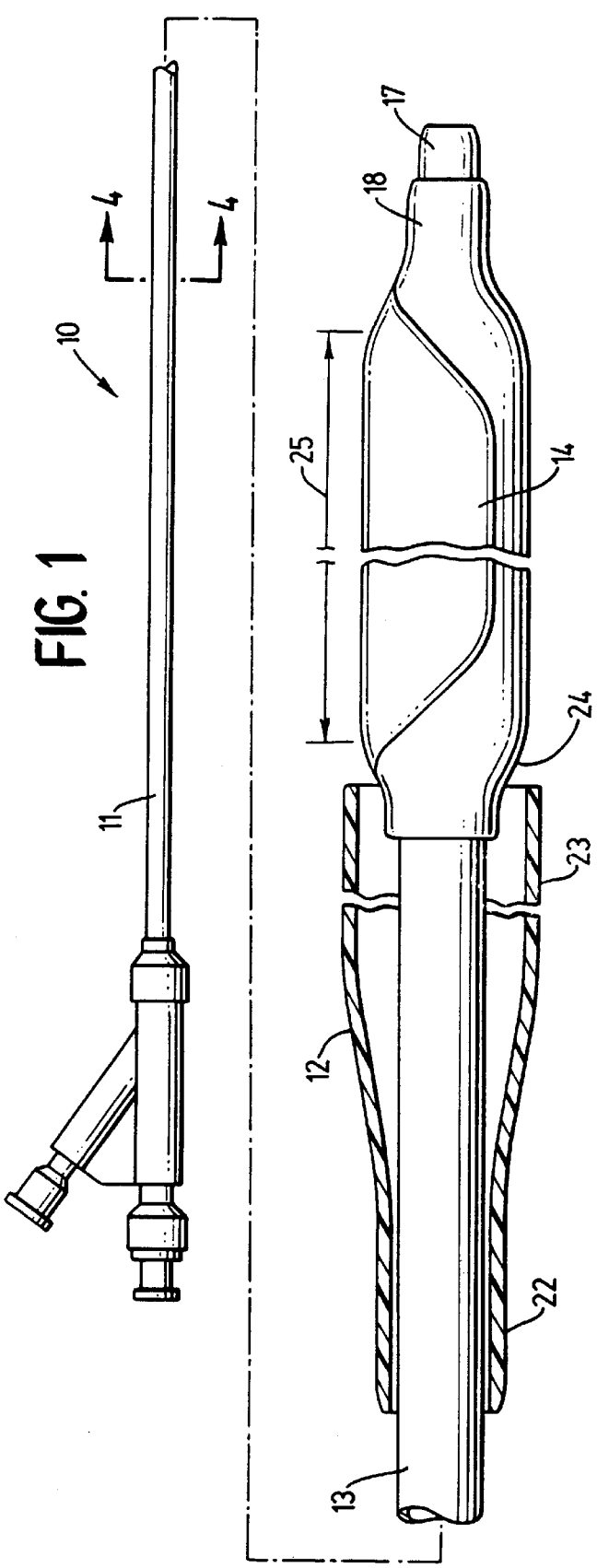
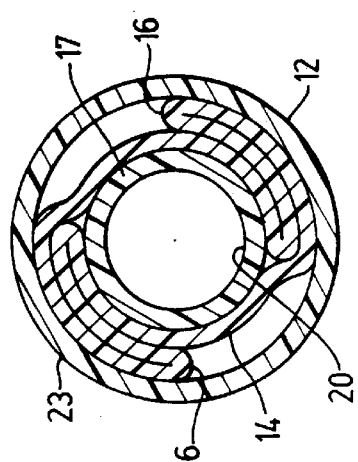
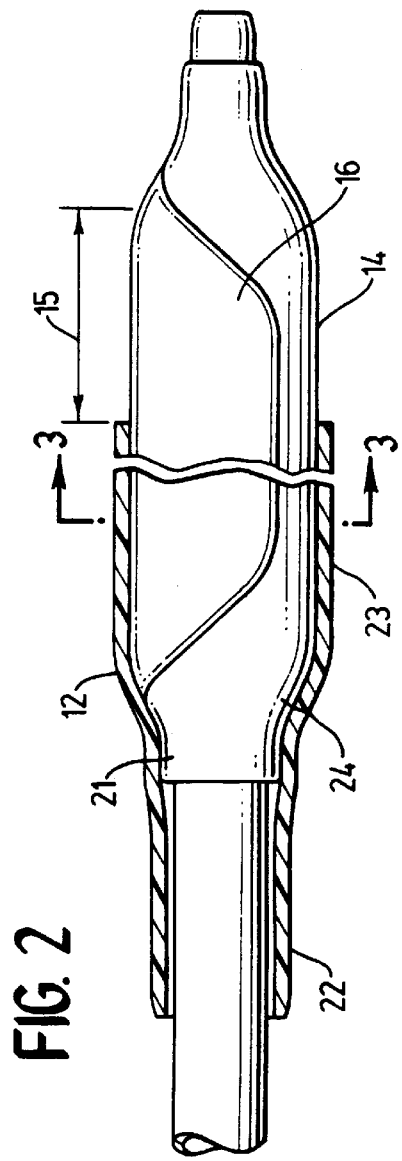

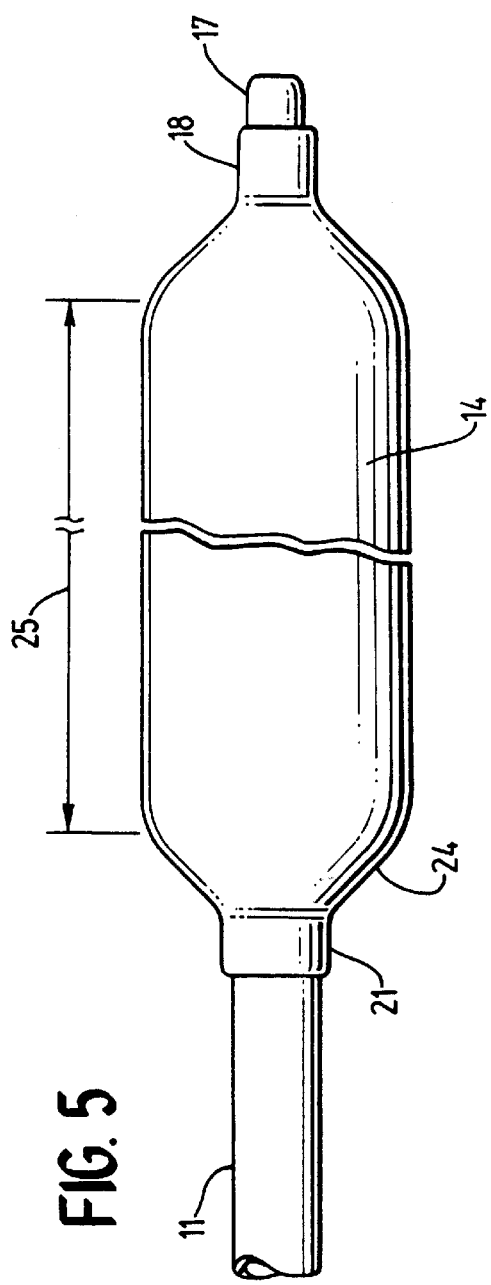
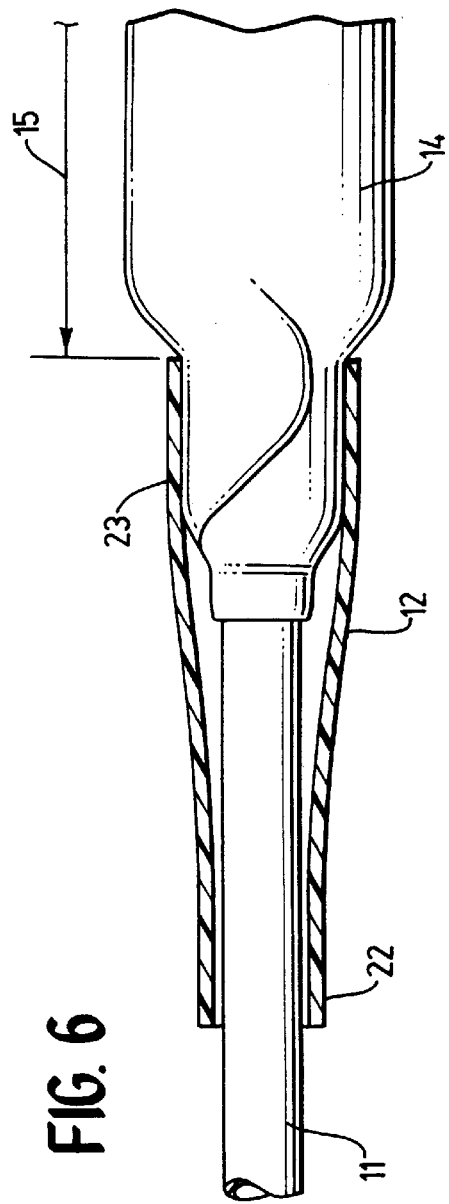
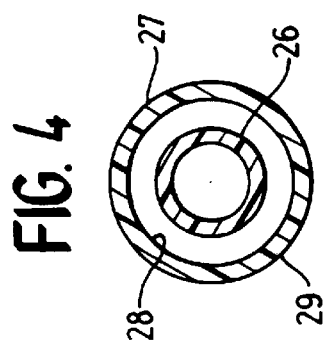

SHEATH FOR AN ADJUSTABLE LENGTH BALLOON

This application is a continuation, of application Ser. No. 08/486,385, filed Jun. 7, 1995.

BACKGROUND OF THE INVENTION

This invention generally relates to intravascular catheters, particularly dilatation catheters for percutaneous transluminal coronary angioplasty.

In typical PTCA procedures, a guiding catheter having a preshaped distal tip is percutaneously introduced by conventional Seldinger techniques into the vascular system of a patient and advanced within the system until the preshaped distal tip of the guiding catheter is disposed within the ascending aorta adjacent the ostium of the desired coronary artery. The guiding catheter is relatively stiff because it has to be twisted or torqued from its proximal end, which extends outside the patient, to turn the distal tip of the guiding catheter so that it can be guided into the desired coronary ostium. A balloon dilatation catheter is introduced into and advanced through the guiding catheter and out the distal tip thereof into the patient's coronary artery until the balloon on the distal extremity of the dilatation catheter is properly positioned across the lesion to be dilated. Once properly positioned, the balloon is inflated one or more times to a predetermined size with radiopaque liquid at relatively high pressures (e.g., generally 4–12 atmospheres) to dilate the stenotic region of the diseased artery. When the dilatations have been completed, the dilatation catheter can be removed from the dilated stenosis to allow the resumption of blood flow through the dilated artery.

There are several types of balloon dilatation catheters which are now widely available, including over-the-wire catheters, fixed-wire catheters, rapid exchange type catheters (which are a type of over-the-wire catheter) and perfusion type catheters (which may be either over-the-wire or rapid exchange type catheters).

Commercially available dilatation catheters typically have balloons with working lengths of 2 cm. Longer balloons, e.g. 3 and 4 cm, have become available in the marketplace to dilate longer lesions so that multiple dilatations along the length of the lesion are not necessary for complete dilatation. However, this increases the number of catheters which must be kept available during a dilatation, because frequently it is not known before the procedure begins how long the lesion is.

Saab in U.S. Pat. No. 5,246,421 discloses an elongated sheath which extends over a long balloon and is adjustable therewith so that only a desired length of balloon which extends distally out of the sheath expands when the balloon is inflated. However, as described, the elongated sheath extends along most of the catheter length, adding both to the profile and the stiffness of the catheter assembly. What has been needed and heretofore unavailable is a dilatation catheter with an adjustable length balloon which does not significantly increase the profile and stiffness of the catheter assembly over the profile and thickness of commercially available products. The present invention satisfies this and other needs as will be described hereinafter.

SUMMARY OF THE INVENTION

The present invention is directed to a dilatation catheter assembly which provides a low profile, flexible dilatation balloon with a variable working length to accommodate a wide variety of stenotic lengths.

The dilatation catheter assembly of the present invention has a dilatation catheter with an elongated shaft, a dilatation balloon on a distal portion of the shaft and a relatively short balloon sheath which is securable at a desired location on the catheter shaft with the sheath extending over a part or all of the dilatation balloon. The short balloon sheath is secured at the desired position on the catheter shaft before it is introduced into the patient. The desired sheath position is selected so that the sheath extends over the balloon to prevent a length of the balloon which is covered by the sheath from expanding when inflation fluid is introduced under pressure into the interior of the balloon, but a length of the balloon which extends out the distal end of the sheath, i.e. is uncovered, is expanded when inflation fluid is introduced into the balloon interior. The length of exposed balloon is usually chosen to correspond to, or overlap the length of the lesion to be dilatated.

The elongated catheter shaft has proximal and distal ends, a first inner lumen extending within at least a distal portion of the catheter shaft to a guidewire port in the distal end of the shaft, a second inner lumen extending from the proximal end of the shaft to a location spaced proximally from the distal tip of the shaft and in fluid communication with the interior of the inflatable dilatation balloon on the distal portion of the catheter shaft.

The balloon sheath has an inner lumen extending along the length thereof with a distal extremity configured to envelop a desired length of the inflatable dilatation balloon in a deflated condition. Preferably, the inner lumen of the distal extremity of the sheath is sufficiently long to cover at least one-half, and preferably the entire working length of the balloon, i.e. the cylindrical portion of the balloon between the balloon tapers and has sufficient diameter to readily receive the balloon in a deflated condition. The sheath/dilatation catheter assembly is configured so that initially the sheath and the dilatation catheter are longitudinally moveable with respect to each other, but means are provided to fix the position of the sheath with respect to the catheter when the assembly is outside the patient so that the desired length of balloon can be exposed before insertion into the patient, but in a manner so that the sheath will resist movement during advancement within the patient's vasculature or during the intravascular procedure.

A variety of means may be employed to secure the sheath with respect to the catheter. For example, the sheath may be configured to have a friction fit with the catheter shaft or the balloon or both of a magnitude which allows manual movement before the procedure but which prevents movement within the patient from frictional forces to which the device is subjected therein. Other means include bonding the proximal portion of the balloon sheath to the catheter shaft after the sheath is in the desired position by the use of an adhesive, by fusion bonding (heat or laser) or by mechanical bonding. Additional means include shaping the inner lumen of the sheath and the exterior or the catheter shaft so that rotation of one of the members with respect to the other will result in a frictional fit therebetween, e.g. both being oval shaped. A variety of other means can be employed for fixing the position of the sheath with respect to the catheter so as to expose a desired length of the dilatation balloon which will expand when inflated but to cover a length of the dilatation balloon which will not expand when the balloon is inflated. The means for fixing the position of the balloon must be functional after the sheath is placed in the desired position but before the assembly is introduced into the patient's vasculature.

The sheath which extends over the balloon should have sufficient strength to prevent the portion of the dilatation balloon over which it extends from expanding. Generally, the sheath can be made of high strength polymer materials such as high density polyethylene, polyethylene therephthalate, ionomers and other materials from which dilatation balloons are made. The sheath should not, however, be so stiff that it detrimentally effects the tracking of the dilatation catheter over the guidewire which the catheter is advanced through the patient's coronary artery. The distal end of the sheath may be provided with a short elastically expandable element which expands to the shape of the proximal end of the expanded balloon portion.

One way of providing the sheath with sufficient longitudinal flexibility, so that tracking of the catheter is not impaired while maintaining sufficient radial rigidity to prevent expansion of the sheath when the balloon is inflated, is to provide, along the length of an otherwise flexible, elastic sheath which is to cover the balloon, a plurality of longitudinally spaced circular bands which are made of high strength relatively inelastic polymer material such as biaxially oriented polyethylene terephthalate. The length of the sheath for the most part remains as longitudinally flexible as without the bands, but the bands effectively prevent significant radial expansion of the portion of the balloon which is covered by the sheath.

Another way to provide the sheath with longitudinal flexibility and radial inelasticity is to form the sheath out of flexible or elastic polymeric material with reinforcing inelastic strands within the matrix of the polymeric material which provide a minimum expansion to an otherwise elastically expandable sheath. The inelastic reinforcing fibrous strands may be braided, wound or otherwise positioned within the polymer matrix to restrict the radial expansion thereof.

The catheter assembly of the invention is used in essentially the same manner as a conventional dilatation catheter, with the assembly being advanced through a guiding catheter which has its distal end seated within the desired coronary ostium and out the end of the guiding catheter into the patient's coronary artery until the distal end of the assembly is disposed proximal to the stenosis to be dilated, as described in the BACKGROUND OF THE INVENTION. The length of the stenotic region is determined by angiography or other means before the angioplasty catheter is inserted into the patient so that the length of exposed working surface of the dilatation balloon can be adjusted according to the length of the stenosis to be dilated. The catheter assembly is then advanced through the guiding catheter and out the distal end thereof into the desired coronary artery until the exposed portion of the dilatation balloon is disposed within the stenotic region so that, when it is inflated, essentially the entire length or at least a much greater length of the stenotic region is dilated.

The catheter of the invention provides a single catheter assembly which can be used to dilate stenoses of a wide range of lengths by merely adjusting the exposed length of the balloon before the assembly is inserted into the patient. Neither the profile of the dilating portion of the balloon nor the flexibility thereof is significantly affected by the use of the short sheath. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a catheter assembly embodying features of the invention with the balloon sheath proximal to the balloon.

FIG. 2 is an elevational view, partially in section, of the distal portion of the assembly shown in FIG. 1 with the balloon sheath disposed partially over the balloon.

FIG. 3 is a transverse cross-sectional view of the assembly shown in FIG. 2 taken along the lines 3—3.

FIG. 4 is a transverse cross-sectional view of the assembly shown in FIG. 1 taken along the lines 4—4.

FIG. 5 is an elevational view of the distal portion of the catheter shown in FIG. 1 with the balloon inflated.

FIG. 6 is an elevational view of the distal portion of the assembly as shown in FIG. 2 with the exposed portion of the balloon in an inflated condition.

DETAILED DESCRIPTION OF THE INVENTION

Figure 7:
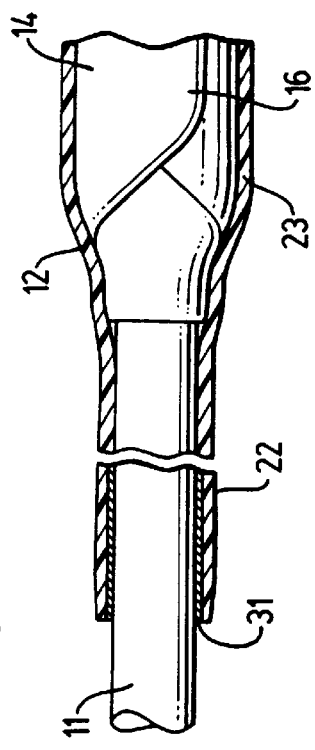
FIG. 7 is an elevational view, partially in section, of the distal portion of the assembly shown in FIG. 1 with a band about the proximal end of the sheath to secure the sheath to the catheter shaft.

FIGS. 1–4 generally illustrate a catheter assembly 10 embodying features of the invention. The assembly 10 includes a balloon dilatation catheter 11 and a balloon sheath 12 slidably mounted on the catheter shaft 13. In FIG. 1 the sheath 12 is shown proximal to the dilatation balloon 14, but in FIG. 2 the sheath is shown disposed over the balloon with a length 15 not covered by the sheath. As illustrated in FIG. 3, the balloon 14 has a pair of wings 16 which are folded about the inner tubular member 17 extending through the interior of the balloon. The distal skirt 18 of the balloon 14 is bonded in a suitable manner to the distal extremity of the inner tubular member 17. The inner tubular member 17 has an inner lumen 20 through which a guidewire (not shown) is slidably disposed in a conventional fashion. The proximal skirt 21 of the balloon 14 is bonded to the exterior of the catheter shaft 11.

The sheath 12 is configured so as to be slidable over the catheter shaft 13 and over the deflated and folded balloon 14. Preferably, the distal portion 23 of the sheath 12 has a length equivalent to the combined length of proximal taper 24 and the working length 25 of the balloon 14 as shown in FIG. 5. FIG. 6 illustrates the balloon 14 in an inflated condition with the exposed length 15 of the balloon expanded to a diameter for dilatation.

The details of the catheter shaft 13 is provided in the transverse cross-section shown in FIG. 4. Generally the shaft 11 may include an inner tubular member 26 and outer tubular member 27 disposed about the inner tubular member and defining an annular inflation lumen 28 between the interior of the outer tubular member and the exterior of the inner tubular member. The inner tubular member 26 may extend to the distal end of the catheter and form the inner tubular member 17. The inner lumen 29 extends distally and becomes inner lumen 20.

Figure 8:
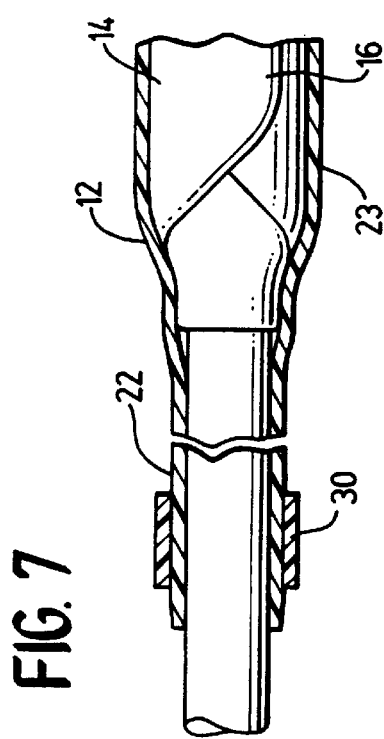
FIG. 8 is an elevational view, partially in section, of the distal portion of the assembly shown in FIG. 1 with the proximal end of the sheath secured by an adhesive or fusion bond to the catheter shaft.

A variety of means may be employed to secure the sheath so that once positioned at the desired location it will not move when the assembly is introduce into and advanced through the patient's vasculature to the desire location therein. As shown in FIG. 7, the proximal portion 22 of the sheath 12 is secured to the catheter shaft 11 by means of a band 30 which is tightly mounted thereon. The band 30 is preferably a plastic band to hold the sheath in position which is either elastic in nature or has been heat shrunk onto the proximal portion 22. In FIG. 8, the proximal portion 22 of the sheath 12 is bonded to the catheter shaft 11 at interface 31. The bond may be made by a suitable adhesive or by fusion bonding such as with heat or laser energy. Other means include a friction fit between the sheath 12 and the shaft 11 which allows manual movement but is secured enough to prevent relative movement when the device is being used.

Figure 9:
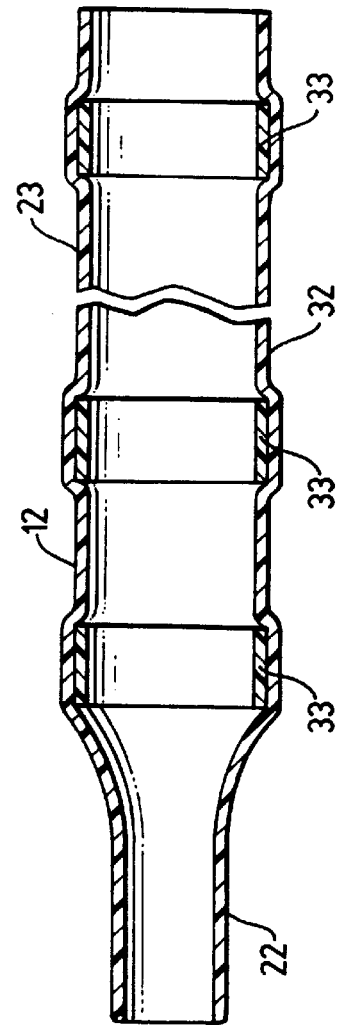
FIG. 9 is a longitudinal cross-sectional view of a presently preferred sheath.

FIG. 9 illustrates one presently preferred embodiment wherein the sheath 12 is formed of a flexible polymer tube 32, e.g. polyethylene, and a plurality of reinforcing rings 33 formed of an inelastic polymer material such as polyethylene terephthalate. The sheath may be formed by placing the reinforcing rings on a suitably configured mandrel and then heat shrinking the polymer tube onto the mandrel.

Figure 10:
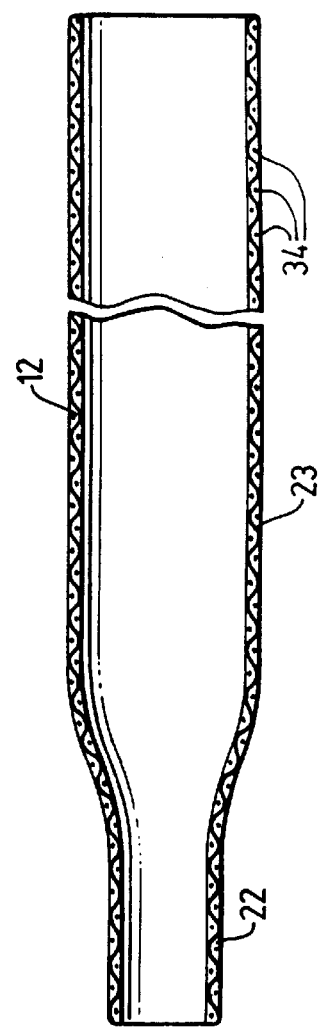
FIG. 10 is a longitudinal cross-sectional view of another presently preferred sheath.

An alternative embodiment of sheath 12 is depicted in FIG. 10 which is formed having inelastic reinforcing strands 34 in the distal section 23 which extends over the balloon. The polymer sheath may be formed of polyethylene or other suitable polymers and the reinforcing strands 34 may be formed of materials such as Kevlar® which is available from Dupont. Other inelastic materials may be used for strands, including metals such as stainless steel and pseudoelastic or shape memory NiTi alloys, commonly called NITINOL. The reinforcing strands may be braided, wound or otherwise placed within the polymer matrix of the distal portion 23 of the sheath 12 to allow for substantial flexibility of the sheath, while preventing substantial expansion thereof when a dilatation balloon disposed therein is inflated.

The length of the distal portion 23 of the sheath 12 may range from about 1 to about 4 cm or more depending upon the working length of the balloon. Dilatation balloons having working lengths ranging from about 1 to about 4 cm are commercially available, and interest has been recently expressed for even longer balloons. The sheath 12 generally should be able to extend over a substantial portion of the working length 25 of the balloon 14. The inner diameter of the distal portion 23 of the sheath 12 should be adequate to accommodate the balloon 14 and generally will range from about 0.02 to about 0.1 inch (0.5–2.5 mm), preferably about 0.03–0.07 inch (0.76–1.77 mm). The sheath 12 should be configured to readily slide over the balloon 14 in a deflated and folded condition.

Although individual features of embodiments of the invention may be shown in some of the drawings and not in others, those skilled in the art will recognize that individual features of one embodiment of the invention can be combined with any or all the features of another embodiment. Additionally, although the invention is described herein in terms of certain preferred embodiments, those skilled in the art will recognize that various modifications can be made to the present invention without departing from the scope thereof.

What is claimed is:

1. A balloon catheter assembly for use in a vascular system, said assembly comprising:
a balloon catheter having an elongated catheter shaft, an inflation lumen extending within the catheter shaft to a location on a distal portion of the shaft and an inflatable balloon mounted on the distal portion of the catheter shaft having an interior in fluid communication with the inflation lumen; and
a balloon sheath which has a length substantially less than the length of the catheter shaft, and an inner lumen in at least a distal sheath portion configured to receive the balloon, the sheath mounted to the catheter shaft and secured thereto by a friction fit, wherein the sheath is sized and adapted for:
slidable movement along the shaft and locking in position on the shaft while the balloon and sheath are outside the vascular system such that the distal sheath portion can be positioned to extend distally over at least a portion of the balloon
such that when the balloon is inflated the sheath remains locked in position and cannot move along the shaft, the sheath configured to prevent expansion of the portion of the balloon over which the sheath extends when the balloon is inflated.

2. The assembly of claim 1 wherein a distal sheath portion is long enough to extend over the entire working length of the balloon.

3. The assembly of claim 2 wherein the balloon has a length of about 1 to about 10 cm.

4. The assembly of claim 1 wherein the inner lumen in a distal sheath portion has a diameter of about 0.02 to about 0.1 inch.

5. The assembly of claim 1 wherein the inner lumen in a distal sheath portion has a diameter of about 0.03 to about 0.07 inch.

6. A balloon catheter assembly for use in a vascular system, said assembly comprising:
a balloon catheter having an elongated catheter shaft, an inflation lumen extending within the catheter shaft to a location on a distal portion of the shaft and an inflatable balloon mounted on the distal portion of the catheter shaft having an interior in fluid communication with the inflation lumen; and
a balloon sheath which has a length substantially less than the length of the catheter shaft, and an inner lumen in at least a distal sheath portion configured to receive the balloon, wherein at least a distal sheath portion is formed of flexible polymeric tube with inelastic reinforcement which prevents the expansion of the distal sheath portion, wherein the sheath is mounted to the catheter shaft and sized and adapted for:
slidable movement along the shaft and locking in position on the shaft while the balloon and sheath are outside the vascular system such that the distal sheath portion can be positioned to extend distally over at least a portion of the balloon such that when the balloon is inflated the sheath remains locked in position and cannot move along the shaft, the sheath configured to prevent expansion of the portion of the balloon over which the sheath extends when the balloon is inflated.

7. The assembly of claim 6 wherein the sheath is bonded to the catheter shaft by an adhesive bond.

8. The assembly of claim 6 wherein the sheath is fusion bonded to the catheter shaft.

9. The assembly of claim 6 wherein the sheath is secured to the catheter shaft by a band about the exterior of the proximal sheath portion.

10. The assembly of claim 6 wherein the inelastic reinforcement is a plurality of inelastic reinforcing rings longitudinally spaced along said distal sheath portion.

11. The assembly of claim 6 wherein the inelastic reinforcing is braided or wound inelastic strands.

12. A balloon catheter assembly comprising:
a balloon catheter having an elongated catheter shaft, an inflation lumen extending within the catheter shaft to a location on a distal portion of the shaft and an inflatable balloon mounted on the distal portion of the catheter shaft having an interior in fluid communication with the inflation lumen; and a balloon sheath which has a length substantially less than the length of the catheter shaft, and an inner lumen in at least a distal sheath portion configured to receive the balloon, the sheath mounted to the catheter shaft and adapted for initial slidable movement along the shaft and subsequent locking in position on the shaft such that the distal sheath portion extends distally over at least a portion of the balloon and remains in position when the balloon is inflated, the sheath configured to prevent the expansion of the portion of the balloon over which the sheath extends when the balloon is inflated;

wherein both the catheter shaft and the inner lumen of the sheath have oval cross sections and the sheath is locked in position on the catheter shaft by rotation of the sheath relative to the shaft.

* * * * *